(12) United States Patent
Ochampaugh

(10) Patent No.: US 8,621,780 B2
(45) Date of Patent: Jan. 7, 2014

(54) SEED INDEX SYSTEM FOR TREATING AGRICULTURAL SEEDS

(75) Inventor: Jeff Ochampaugh, Russell, KS (US)

(73) Assignee: Agrilead, Inc., Russell, KS (US)

( * ) Notice: Subject to any disclaimer, the term of this patent is extended or adjusted under 35 U.S.C. 154(b) by 117 days.

(21) Appl. No.: 13/269,694

(22) Filed: Oct. 10, 2011

(65) Prior Publication Data

US 2012/0115911 A1     May 10, 2012

Related U.S. Application Data

(60) Provisional application No. 61/411,783, filed on Nov. 9, 2010.

(51) Int. Cl.
*A01C 1/06* (2006.01)

(52) U.S. Cl.
CPC ........................................ *A01C 1/06* (2013.01)
USPC ........................................ 47/58.1 SE; 47/57.6

(58) Field of Classification Search
CPC ...................................................... A01C 1/02
USPC ............................................ 47/58.1 SE, 57.6
See application file for complete search history.

(56) References Cited

U.S. PATENT DOCUMENTS

| | | | |
|---|---|---|---|
| 2,502,809 A | 2/1944 | Vogelsang |
| 4,936,978 A | 6/1990 | Bortnikov et al. |
| 6,186,194 B1 | 2/2001 | Poupon |
| 7,869,902 B2 | 1/2011 | Hunter et al. |
| 2008/0009962 A1 | 1/2008 | Hood et al. |

OTHER PUBLICATIONS

Yleef; Seed treatment costs 50 lb vs. 140000 units, Forums List -→ Crop Talk; Ag Talk; http://talk.newagtalk.com/forums/thread-view.asp?tid=161818&mid=1161908; Posted Apr. 14, 2010 07:32 (#1161908—in reply to #1161494).
Use and Mixing, Poncho VOTiVO; Seed Treatments Products; http://www.bayercropscience.us/products/seed-treatments/poncho-votivo/use-mixing; Bayer CropScience, United States; 2011.
Crown Solution: A combination systemic and contact seed protectant for use on lentils and chickpeas. Crown provides control of seed-borne ascochyta (*Ascochyta rabiei*) on chickpeas; Chemtura Canada Co./Cie, 25 Erb Street, Elmira, Ontario N3B3A3; Jul. 14, 2010; 2009-4301; pp. 1-5.
Scott D. Stewart (editor); IPM Newsletter: Update for Field Crops and Their Pests; Apr. 25, 2003; pp. 1-4; vol. No. 2; Agricultural Extension Service, The University of Tennessee, Jackson, TN.
Flo Rite 1197: Plantability Polymer; Becker Underwood, Inc.; Amers, IA; pp. 1-2; Rev. Jan. 2011.
Seed Treating Accessories; USC Seed Treating Solutions; Universal Seed Care; Sabetha, Kansas; uscllc.com; 02 Rev. 2011 USC, LLC.
Tracy Sayler, Dynasty Seed Treatment Adjusted, 2 pages, Dec. 2006, Sunflower Magazine, US.†
Nitrogen Fixation for Tropical Agricultural Legumes (NifTAL) Project, USA, et al., Legume Inoculants and Their Use, 75 pages, 1984, Food and Agriculture Organization of the United Nations, Rome.†
US Environmental Protection Agency, Notice of Pesticide Registration, 6 pages, May 30, 2003, US Environmental Protection Agency, Washington D.C.†

† cited by third party

*Primary Examiner* — Kristen C Hayes
(74) *Attorney, Agent, or Firm* — Hovey Williams LLP

(57) ABSTRACT

Seed index system and methods for treating agricultural seeds with one or more seed care products employing a size-adjusted application rate based on the size of the seeds. Such size-adjusted application rates can be determined by a supplier of seed care products and communicated to an applicator who applies the seed care product to a quantity of seeds. Such size-adjusted application rates can be in the form of a chart, an equation, or a calculator.

35 Claims, 1 Drawing Sheet

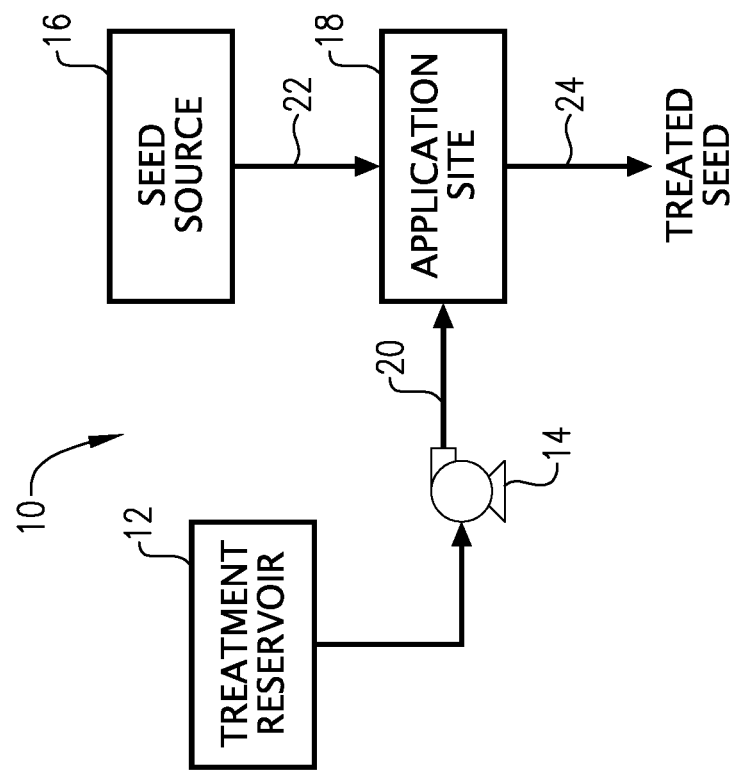

SEED INDEX SYSTEM FOR TREATING AGRICULTURAL SEEDS

RELATED APPLICATIONS

This application claims the priority benefit under 35 U.S.C. §119(e) of U.S. Provisional Patent Application Ser. No. 61/411,783 entitled "SEED INDEX SYSTEM FOR TREATING AGRICULTURAL SEEDS," filed Nov. 9, 2010, the entire disclosure of which is incorporated herein by reference.

BACKGROUND

1. Field of the Invention

Various embodiments of the present invention relate to systems and methods for treating agricultural seed. More specifically, certain embodiments of the present invention relate to systems and methods for treating agricultural seed based on seed size.

2. Description of the Related Art

Manufacturers of seed-applied fungicides, insecticides, and other seed care products have traditionally expressed application rates of such products based on a measured weight of the seed being treated. Most traditionally, these rates have been expressed as a rate of liquid or dry ounces to be applied per 100 pounds ("cwt") of seed. However, this traditional method of rate expression delivers a widely varied application rate of active ingredients per seed depending on the size of the seed being treated. Accordingly, improvements are needed in the seed-treating industry.

SUMMARY

One embodiment of the present invention concerns a seed treatment method comprising: (a) obtaining a quantity of seeds from a seed supplier; (b) obtaining a seed care product from a seed care product supplier; (c) determining a size-adjusted application rate at which to apply the seed care product to the quantity of seeds, where the size-adjusted application rate is based on the seed size of the seeds; and (d) applying at least a portion of the seed care product to at least a portion of the seeds at the size-adjusted application rate to thereby provide treated seeds.

Another embodiment of the present invention concerns a method of providing a seed care product. The method of this embodiment comprises: (a) obtaining a seed care product; (b) determining a plurality of size-adjusted application rates for applying the seed care product to seeds, wherein the size-adjusted application rate is based on the size of the seeds; (c) providing the seed care product to an applicator of seed care products; and (d) communicating the size-adjusted application rates to the applicator of seed care products.

Still another embodiment of the present invention concerns a seed treatment method comprising: (a) obtaining a quantity of seeds from a seed supplier; (b) obtaining a seed care product from a seed care product supplier; (c) determining a size-adjusted application rate at which to apply the seed care product to the seeds, wherein the size-adjusted application rate is based on the seed size of the seeds; and (d) applying at least a portion of the seed care product to at least a portion of the seeds at the size-adjusted application rate to thereby provide treated seeds. In this embodiment, the seed size is based either on the number of the quantity of seeds per a selected unit of weight or by physical measurement of the size of at least a portion of the quantity of seeds.

BRIEF DESCRIPTION OF THE FIGURES

Embodiments of the present invention are described herein with reference to the following drawing FIGURE, wherein:

FIG. 1 is a schematic illustration of a seed-treating system for treating seeds with one or more seed care products according to an embodiment of the present invention, particularly illustrating a seed treatment reservoir, a seed source, and an application site.

DETAILED DESCRIPTION

Various embodiments of the present invention concern methods for treating agricultural seed with various types of seed care products or treatments. As used herein, the term seed "treatment" may be used both as a noun to generically refer to various types of seed care products as well as a verb to describe the process by which seed care products are applied to agricultural seed. In certain embodiments, methods are provided for adjusting seed treatment application rates to agricultural seed based on the seed size of the seed. Such methods may include the steps of (a) obtaining a quantity of seeds; (b) obtaining a seed care product; (c) determining a size-adjusted application rate at which to apply the seed care product to the seeds, where the size-adjusted application rate is based on the seed size of the seeds; and (d) applying the seed care product to the seeds.

As just noted, an initial step in the methods described herein can be to obtain a quantity of seeds. Any seeds known or hereafter discovered in the art can be employed in the various embodiments described herein. In one or more embodiments, the seeds can be agricultural-type seeds. Examples of seeds suitable for use include, but are not limited to, soybeans, alfalfa, canola, corn, sorghum, sugarbeets, wheat, barley, oats, rice, cotton, and sunflowers. Additionally, such seeds can be obtained from a supplier of agricultural seeds. Examples of suitable commercial seed suppliers include, but are not limited to, Monsanto, Albaugh, Bayer Crop Science, BASF, Chemtura, Nufarm, Syngenta, and Valent.

As noted above, a seed care product (a.k.a., treatment) can be selected for application to the seed. Any seed treatments known or hereafter discovered in the art can be employed in the various embodiments described herein. For example, suitable seed treatments can include a fungicide, an insecticide, a nematicide, a rodenticide, a plant growth regulator, a nutritional, a growth enhancer, a dye, a colorant, a flow control agent, a dust control agent, an encrusting agent, a pelleting agent, or mixtures of two or more thereof. In various embodiments, a plurality of such seed treatments can be applied to the seed. Additionally, seed treatments can be in the form of a solid (e.g., a dry powder) or a liquid (e.g., a solution, suspension, or slurry). Commercially available examples of such seed care products include, but are not limited to, MACHO 600ST from Albaugh, TRILEX 2000 from Bayer Crop Science, ALLEGIANCE FS from Bayer Crop Science, GAUCHO 600 FS from Bayer Crop Science, GAUCHO XT from Bayer Crop Science, RAXIL MD from Bayer Crop Science, AXCESS from BASF, ACQUIRE from BASF, STAMINA from BASF, CHARTER from BASF, RANCONA 3.8FS from Chemtura, ATTENDENT 480FS from Chemtura, BELMONT 2.7FS from Chemtura, SENATOR 600 FS from Nufarm, SEBRING 2.65 ST from Nufarm, SATIVA M RTU from Nufarm, SATIVA IM Max from Nufarm, APRON XL from Sygenta, APRON MAXX RFC from Sygenta, CRUISER MAXX BEANS from Sygenta, CRUISER SFS from Sygenta, DIVIDEND EXTREME from Sygenta, MAXIM 4FS from Sygenta, NIPSIT INSIDE from Valent, and RANCONA EXTRA from Valent.

In various embodiments, the seed treatment or treatments selected for use can be manufactured by the same entity that applies the seed treatment to the selected seed, as described below. In various other embodiments, the seed treatment producer and the seed treatment applicator can be different entities. For example, as discussed in greater detail below, the applicator of the seed treatment can be a seed distributor, a seed retailer, or a grower (e.g., a farm operation).

As mentioned above, once the seed types and seed treatments have been selected, a size-adjusted application rate can be determined at which to apply the treatment to the seeds, where the size-adjusted application rate can be based on the seed size of the seeds. As used herein, the term "seed size" shall mean any type of determination that correlates to the size of the selected type of seed. For instance, "seed size" can be expressed in terms of the number of seeds per a given unit of weight, the number of seeds per a given unit of volume, or any type of physical measurement of the size of individual seeds. Physical measurement may include any determination of one or more dimensions of individual seeds, such as diameter, circumference, surface area, and the like. In various embodiments, the seed size can be based on the number of seeds per a given unit of weight, such as the number of seeds per pound. In other various embodiments, the seed size can be based on measurements of one or more physical dimensions related to the size of individual seeds.

Furthermore, in certain embodiments, the seed size can be based on an average seed size of the seeds to be treated. For instance, the seed size can be an average of measurements based on a plurality of samples taken from a larger batch of seeds intended to be treated. For example, a portion of seeds can be selected from a larger batch intended for treatment and physically measured for seed size; thereafter, an average of the measurements can be detei mined and employed for selecting a size-adjusted application rate. As another example, a plurality of samples can be taken from a larger batch intended for treatment and counted and weighed to determine the number of seeds per pound in each of the samples; thereafter, an average of the measurements can be determined and employed for selecting a size-adjusted application rate. In other various embodiments, the average seed size can be based on information provided by a supplier of such seeds (e.g., such as through labeling information provided on a commercially supplied quantity of seeds).

The actual seed size of the seeds employed by the methods described herein can vary greatly not only between different types of seed but within the same type of seed. In fact, this variance in seed size within the same type of seed at least partly forms the basis for the embodiments of the present invention described herein. Thus, in various embodiments, the seed size can vary, for example, anywhere from about 1,000 seeds per pound to about 5,000 seeds per pound, from about 1,500 seeds per pound to about 4,500 seeds per pound, or from about 2,000 seeds per pound to about 4,000 seeds per pound.

Once a seed size has been determined for a quantity of seeds to be treated, a size-adjusted application rate can be determined for applying one or more of the above-described seed treatments to the seeds. In one or more embodiments, the size-adjusted application rate can be based on a size index that correlates the seed size to the application rate of the seed treatment. For instance, a size index can correlate a certain seed size (e.g., 2,800 seeds per pound) to a certain amount of seed treatment (e.g., 3.0 fluid ounces of treatment per 100 pounds of seed). Thereafter, variations in seed size can be reflected by variations in the amount of seed treatment. For instance, using the initial size index of 3.0 fluid ounces per 100 pounds of seed for a seed size of 2,800 seeds per pound, a smaller seed size (e.g., 2,100 seeds per pound) could correlate to a smaller treatment application rate (e.g., 2.2495 fluid ounces of treatment per 100 pounds of seed).

Note that there will generally be an inverse relationship between the physical size (e.g., diameter, circumference, and/or surface area) of the individual seeds and the seed treatment application rate. In other words, as the physical size of the individual seeds decreases, the application rate will generally increase. This is due to the fact that seed treatments are primarily concerned with coating the surface area of the seeds. As is well known, as the physical size of the seeds decreases, the number of seeds per a given volume or weight will generally increase; thus, the surface area of such given volume or weight of seeds will increase. Accordingly, as the dimensions of individual seeds decreases, the overall surface area per volume or weight increases, thus resulting in an increased treatment application rate. On the other hand, if the seed size is not expressed in terms of the physical size of individual seeds, the relationship between seed size and seed treatment application rate may be directly proportional. For instance, if seed size is expressed as the number of seeds per pound, then, as the number of seeds per pound increases, so too should the treatment application rate. Accordingly, depending on how seed size and treatment rates are expressed, their relationship may either be directly or inversely proportional.

Treatment application rate variance away from the above-mentioned size index can be determined or provided in a variety of ways. In various embodiments, a supplier of seed care products can determine a plurality of size-adjusted application rates for various seed sizes for such seed care products. These different size-adjusted application rates can then be provided to an applicator of such seed care products, so that the applicator can adjust the application rate of the seed care product depending on the specific seed size of the quantity of seeds to be treated. Additionally, distinct sets of size-adjusted application rates can be provided for a variety of different seed types. For example, one set of size-adjusted application rates could be provided for soybeans while a separate, distinct set of size-adjusted application rates could be provided for corn.

In various embodiments, variation of the treatment application rate may be provided for in a chart. In such an embodiment, a supplier, manufacturer, or applicator of a seed treatment may determine a plurality of seed treatment application rates that correspond to different seed size values. An exemplary Size Index Rate Adjustment ("SIRA") chart, including a reference Size Index ("SI"), is provided below as Table 1:

TABLE 1

Sample SI and SIRA Chart
SIRA

| Seed Size | | fl. oz per 100 lbs of seed |
|---|---|---|
| Seeds per Pound | 2,100 | 2.2495 |
| | 2,200 | 2.3566 |
| | 2,300 | 2.4637 |
| | 2,400 | 2.5708 |
| | 2,500 | 2.6780 |
| | 2,600 | 2.7851 |
| | 2,700 | 2.8922 |

TABLE 1-continued

Sample SI and SIRA Chart

| Seed Size | SIRA fl. oz per 100 lbs of seed | |
|---|---|---|
| 2,800 | 3.0000 | SI |
| 2,900 | 3.1064 | |
| 3,000 | 3.2136 | |
| 3,100 | 3.3207 | |
| 3,200 | 3.4278 | |
| 3,300 | 3.5349 | |
| 3,400 | 3.6420 | |
| 3,500 | 3.7492 | |
| 3,600 | 3.8563 | |
| 3,700 | 3.9634 | |
| 3,800 | 4.0705 | |

In various embodiments, at least one SIRA chart, such as the one shown in Table 1, above, could be included with a commercially purchased seed treatment, such as by the supplier or manufacturer of the seed treatment. Furthermore, in various embodiments, such a SIRA chart could be included as a label affixed to a container containing a seed treatment. In use, such a SIRA chart may be referred to by an applicator of seed treatment in determining the proper seed treatment application rate based on the seed size of the quantity of seeds to be treated.

In other embodiments, the size-adjusted application rate can be determined using a SIRA equation. In such an equation, a size-adjusted application rate can be calculated by inputting the seed size of the quantity of seeds into the SIRA equation and solving for the size-adjusted application rate. For example, using a known Size Index (such as the Size Index indicated in Table 1, above) an adjustment factor can be deduced, resulting in a SIRA equation reading, for example:

[Seed Size]×[Adjustment Factor]=[Size-Adjusted Application Rate]

Such a SIRA equation could be employed to determine the size-adjusted application rate by an applicator knowing the specific seed size of the quantity of seeds to be treated and the adjustment factor. For example, using the SI of 3.000 fl. oz/hundred pounds ("cwt") of seed for a seed size of 2,800 seeds per pound, an adjustment factor of approximately 0.001071 can be deduced. This factor could then be employed with other specific seed sizes to determine a size-adjusted application rate. In various embodiments, a SIRA equation can be provided by a supplier of a seed care product in conjunction with such a seed care product. In such embodiments, an adjustment factor can also be included with the SIRA equation. It should be noted that such adjustment factors need not be simple multiples, but could be complex equations in and of themselves containing more than one variable. In various embodiments, a SIRA equation can be printed on a label and provided with a corresponding seed care product. Furthermore, such a label can be affixed to a container containing the seed care product.

In still other embodiments, a SIRA calculator could be employed to determine the size-adjusted application rate. In such an embodiment, a calculator could be produced or provided to an applicator of the seed treatment in which the seed size of the quantity of seeds to be treated could be inputted to arrive at the size-adjusted application rate. Such a SIRA calculator could be provided in the form of an online calculator that an applicator could access via an internet-capable device. In various embodiments, a SIRA calculator can be provided by a supplier of a seed care product. Directions for using and/or accessing such a SIRA calculator can be printed on a label and provided with a corresponding seed care product. Furthermore, such a label can be affixed to a container containing the seed care product.

The seed care product suppliers in the above-described scenarios can be any type of seed care product supplier in the industry. For instance, such seed care product suppliers could be a manufacturer of the seed care product who produces their own seed care product. Alternatively, the seed care product supplier could be a wholesaler or distributor of the seed care product. In still another alternative, the seed care product supplier could be a retailer who may typically sell directly to the end-user, such as a farm operation, that plants and grows crops from the seeds.

Any of the afore-mentioned parties may perform the application process and employ the above-described treatment methods in treating seeds with a seed care product. Thus, in various embodiments, a manufacturer of seed care products may employ one or more of these methods to treat seeds. In other embodiments, a distributor or wholesaler may employ one or more of these processes to treat seeds. In still other embodiments, a seed and/or seed care product retailer may employ one or more of these processes to treat seeds. In yet other embodiments, a farm operation could employ one or more of these processes to treat seeds, thereafter planting and growing the seeds.

Any system and/or equipment for treating seeds with a seed care product now known or hereafter discovered in the art can be employed in conjunction with the above-described treatment methods. An example of one such treatment system is now described with reference to FIG. 1. As can be seen in FIG. 1, a seed treatment system 10 is shown comprising a treatment reservoir 12, a pump 14, a seed source 16, and an application site 18. In operation, a seed treatment contained in the treatment reservoir 12 can be pumped via pump 14 through line 20 to the application site 18. Similarly, seed from the seed source 16 can be transported via line 22 to the application site, where the incoming seed treatment can be applied. Application of the seed treatment to the seed at application site 18 can be performed by any known or hereafter discovered methods in the art. An example of one such method may involve the use of an atomizer or other spray method for spraying the seed treatment onto the seed when the seed treatment is a liquid. Another example of an application method may be to simply meter in the seed treatment as the seed is flowing into the application site 18. This method may typically be employed with a solid seed treatment. Following application, whether a liquid or a solid seed treatment is employed, the seed and seed treatment may be mixed or tumbled to increase the uniformity of the treatment on the seeds.

Although not depicted, the seed treatment system 10 can also comprise valves or other components employed to control the flow rate of both the seed in the line 22 and the seed treatment in the line 20. Furthermore, flow rate meters may also be employed to provide the applicator an indication of the actual flow rate so the applicator can accurately control the flow rates of both the seed in the line 22 and the seed treatment in the line 20. Thus, in operation, an applicator operating the seed treatment system 10 can calibrate the system to apply the above-described SIRA rate of application based on the size of the seed to be treated using such flow control mechanisms. Such calibration can be achieved by coordinating the volumetric flow of seed treatment to the volumetric flow of the seed. Any known or hereafter discovered methods for controlling and calibrating the flow of seed and seed treatment in the seed treatment system 10 can be employed in the embodiments described herein.

As shown in FIG. 1, after treatment in the application site 18, treated seed can be discharged via a line 24. In various embodiments, the treated seed can have a weight that is not more than 10 percent, not more than 5 percent, not more than 2 percent, or not more than 1 percent greater than the weight of the seeds prior to treatment (i.e., seeds from the seed source 16). Additionally, in various embodiments, the treated seed can be dry enough to handle upon discharge from the application site 18. For example, the treated seed can have a liquid content of less than 10, less than 5, less than 2, less than 1, or less than 0.1 weight percent based on the entire weight of the treated seed upon discharge from the application site 18.

Following treatment in the seed treatment system 10, the treated seed can undergo one or more post-treatment options. Examples of such post-treatments include, but are not limited to, coating, encrusting, and/or pelleting the treated seeds.

This invention can be further illustrated by the following examples of embodiments thereof, although it will be understood that these examples are included merely for the purposes of illustration and are not intended to limit the scope of the invention unless otherwise specifically indicated.

EXAMPLES

Example 1

Conventional Soybean Seed Treatment
(Comparative/Prophetic)

An effective seed treatment application begins with the proper mixing of the seed treatment slurry to be applied to the seed. Ultimately the goal of the application is to deliver efficacious rates of the active ingredients to each and every seed in the treated seed lot. To achieve efficacious distribution of very small amounts of seed treatment active ingredients to large numbers of seed, seed treatment products are typically diluted in the formulation of the product by the manufacturer and then delivered with labeled use instructions at a rate of application that either requires no further dilution (ready-to-apply products) or requires the applicator to dilute the product further with water (tank-mix products). The dilution level then impacts the volume of the mixed treatment slurry to apply per 100 pounds of seed. As each crop seed is different than the other, so are the rates of application coverage required to achieve good distribution of the mixed slurry on the seeds without being too wet to impede the handling of seed after application.

Generally, seed treatment can comprise four steps: (1) determining the seed treatment slurry prescription; (2) mixing the seed treatment slurry based on the prescription; (3) calibrating application equipment; and (4) treatment application.

In the first step, the applicator develops the treatment slurry prescription by selecting products and determining the suggested rate of application from the manufacturer-provided label for each of the products selected. By way of illustration, a sample prescription is provided in Table 2, below:

TABLE 2

Seed Treatment Prescription

| Treatment Product | Purpose | Labeled Rate |
| --- | --- | --- |
| Rancona 3.8 FS | Fungicide | 0.085 fl. oz/cwt |
| Sebring 2.65 | Fungicide | 0.375 fl. oz/cwt |
| Senator 600 FS | Insecticide | 1.600 fl. oz/cwt |

TABLE 2-continued

Seed Treatment Prescription

| Treatment Product | Purpose | Labeled Rate |
| --- | --- | --- |
| Colorant | Treatment and coverage indicator | 0.500 fl. oz/cwt |
| Water rate | Diluent to increase the rate of slurry coverage required to achieve efficacious distribution | 2.440 fl. oz/cwt |
| Total Prescription | | 5.000 fl. oz/cwt |

After determining the desired prescription, the applicator prepares the treatment slurry based on the formulated prescription, taking into consideration the amount of seed to be treated with the slurry. The following Table 3 presents a sample slurry preparation based on the prescription provided above in Table 2 to be used in treating 10,000 pounds of seed.

TABLE 3

Sample Treatment Slurry Preparation

| Treatment Product | No. of CWTs to be Treated | Labeled Rate |
| --- | --- | --- |
| Rancona 3.8 FS | 100 | 8.5 fl. oz |
| Sebring 2.65 | 100 | 37.5 fl. oz |
| Senator 600 FS | 100 | 160.0 fl. oz |
| Colorant | 100 | 50.0 fl. oz |
| Water rate | 100 | 244.0 fl. oz |
| Total Slurry | | 500.0 fl. oz |

Following slurry preparation, the applicator calibrates the application rate by first determining the rate of seed flow in the treatment process. This can be accomplished by taking a known volume of seed, such as a 2,000 pound bulk bag, and running it through the treater without treatment for the purpose of timing the elapsed time for the seed to flow through the treater. With that information, the applicator can then determine the amount of treatment slurry that should be pumped per minute when treating seed to achieve the proper application rate. By way of example, if the time required to pass the desired amount of seed through the treater is 155 seconds, this translates to 7.74 cwt's of seed per minute. Thus, based on the slurry preparation described above, the treater should apply 38.7 fl. oz of treatment slurry per minute to the seed.

Once the treater is calibrated and the flow rates have been determined, the applicator initiates the seed flow and slurry flow simultaneously. The measured amount of seed will then be treated at the rate of calibration. If calibrated correctly, the slurry reservoir and the seed feed bin will empty at the same time, resulting in treated seed.

Example 2

Seed Treatment Variance Due to Seed Size
(Comparative/Prophetic)

Soybeans can vary in seed size from a general range of about 2,100 to as many as about 3,800 seeds per pound or more. As a result of this seed size variance, the number of seeds in a 100 pound sample of soybean seed can range from about 21,000 to about 38,000 seeds. Despite this variance, treatment rate recommendations supplied with commercial seed treatments are expressed as a measured amount of treatment to be applied per a measured weight of seed or volume of seed based on a standard weight per bushel or 50 pound unit. Accordingly, applying seed treatment at the recommended rate can result in a widely varied application rate of active ingredient per individual seed.

Table 4, below, provides a prophetic analysis of how seed treatment can vary depending on seed size when the same application rate is employed across a range of different sized seeds.

TABLE 4

Application Rate Variance Per Seed

| Seeds per Pound | Slurry Application Rate (fl. oz/100 lbs) | | | | | | | | |
|---|---|---|---|---|---|---|---|---|---|
| | 2.25 | 2.50 | 2.75 | 3.00 | 3.25 | 3.50 | 3.75 | 4.00 | |
| 2100 | $3.2E^{-04}$ | $3.5E^{-04}$ | $3.9E^{-04}$ | $4.2E^{-04}$ | $4.6E^{-04}$ | $4.9E^{-04}$ | $5.3E^{-04}$ | $5.6E^{-04}$ | mL Treatment Delivered |
| 2200 | $3.0E^{-04}$ | $3.4E^{-04}$ | $3.7E^{-04}$ | $4.0E^{-04}$ | $4.4E^{-04}$ | $4.7E^{-04}$ | $5.0E^{-04}$ | $5.4E^{-04}$ | per Seed |
| 2300 | $2.9E^{-04}$ | $3.2E^{-04}$ | $3.5E^{-04}$ | $3.8E^{-04}$ | $4.2E^{-04}$ | $1.5E^{-04}$ | $4.8E^{-04}$ | $5.1E^{-04}$ | |
| 2400 | $2.8E^{-04}$ | $3.1E^{-04}$ | $3.4E^{-04}$ | $3.7E^{-04}$ | $4.0E^{-04}$ | $4.3E^{-04}$ | $4.6E^{-04}$ | $4.9E^{-04}$ | |
| 2500 | $2.7E^{-04}$ | $3.0E^{-04}$ | $3.2E^{-04}$ | $3.5E^{-04}$ | $3.8E^{-04}$ | $4.1E^{-04}$ | $4.4E^{-04}$ | $4.7E^{-04}$ | |
| 2600 | $2.6E^{-04}$ | $2.8E^{-04}$ | $3.1E^{-04}$ | $3.4E^{-04}$ | $3.7E^{-04}$ | $4.0E^{-04}$ | $4.3E^{-04}$ | $4.5E^{-04}$ | |
| 2700 | $2.5E^{-04}$ | $2.7E^{-04}$ | $3.0E^{-04}$ | $3.3E^{-04}$ | $3.6E^{-04}$ | $3.8E^{-04}$ | $4.1E^{-04}$ | $4.4E^{-04}$ | |
| 2800 | $2.4E^{-04}$ | $2.6E^{-04}$ | $2.9E^{-04}$ | $3.2E^{-04}$ | $3.4E^{-04}$ | $3.7E^{-04}$ | $4.0E^{-04}$ | $4.2E^{-04}$ | |
| 2900 | $2.3E^{-04}$ | $2.5E^{-04}$ | $2.8E^{-04}$ | $3.1E^{-04}$ | $3.3E^{-04}$ | $3.6E^{-04}$ | $3.8E^{-04}$ | $4.1E^{-04}$ | |
| 3000 | $2.2E^{-04}$ | $2.5E^{-04}$ | $2.7E^{-04}$ | $3.0E^{-04}$ | $3.2E^{-04}$ | $3.4E^{-04}$ | $3.7E^{-04}$ | $3.9E^{-04}$ | |
| 3100 | $2.1E^{-04}$ | $2.4E^{-04}$ | $2.6E^{-04}$ | $2.9E^{-04}$ | $3.1E^{-04}$ | $3.3E^{-04}$ | $3.6E^{-04}$ | $3.8E^{-04}$ | |
| 3200 | $2.1E^{-04}$ | $2.3E^{-04}$ | $2.5E^{-04}$ | $2.8E^{-04}$ | $3.0E^{-04}$ | $3.2E^{-04}$ | $3.5E^{-04}$ | $3.7E^{-04}$ | |
| 3300 | $2.0E^{-04}$ | $2.2E^{-04}$ | $2.5E^{-04}$ | $2.7E^{-04}$ | $2.9E^{-04}$ | $3.1E^{-04}$ | $3.4E^{-04}$ | $3.6E^{-04}$ | |
| 3400 | $2.0E^{-04}$ | $2.2E^{-04}$ | $2.4E^{-04}$ | $2.6E^{-04}$ | $2.8E^{-04}$ | $3.0E^{-04}$ | $3.3E^{-04}$ | $3.5E^{-04}$ | |
| 3500 | $1.9E^{-04}$ | $2.1E^{-04}$ | $2.3E^{-04}$ | $2.5E^{-04}$ | $2.7E^{-04}$ | $3.0E^{-04}$ | $3.2E^{-04}$ | $3.4E^{-04}$ | |
| 3600 | $1.8E^{-04}$ | $2.0E^{-04}$ | $2.3E^{-04}$ | $2.5E^{-04}$ | $2.7E^{-04}$ | $2.9E^{-04}$ | $3.1E^{-04}$ | $3.3E^{-04}$ | |
| 3700 | $1.8E^{-04}$ | $2.0E^{-04}$ | $2.2E^{-04}$ | $2.4E^{-04}$ | $2.6E^{-04}$ | $2.8E^{-04}$ | $3.0E^{-04}$ | $3.2E^{-04}$ | |
| 3800 | $1.7E^{-04}$ | $1.9E^{-04}$ | $2.1E^{-04}$ | $2.3E^{-04}$ | $2.5E^{-04}$ | $2.7E^{-04}$ | $2.9E^{-04}$ | $3.1E^{-04}$ | |

As can be seen from the calculated data provided in Table 4, above, at a given slurry application rate using a prescribed treatment amount based solely on the weight of the seeds, the amount of treatment delivered on a per-seed basis can vary significantly. As a specific example, using a slurry application rate of 3.00 fl. oz per 100 pounds of seed at 2,300 seeds per pound gives a treatment per seed rate of 0.00038 mL/seed. By comparison, a slurry application rate of 3.00 fl. oz per 100 pounds of seed at 3,600 seeds per pound gives a treatment per seed rate of 0.00025 mL/seed. This represents a greater than 50 percent increase in treatment per seed for the seed size of 2,300 seeds per pound compared to the seed size of 3,600 seeds per pound.

Example 3

Implementation of Size Indexed Rate Adjustment (Inventive/Prophetic)

The following prophetic example provides a description of how seed treating operations can be performed from three different perspectives using Size Indexed Rate Adjustment to treat seeds accounting for seed size variance. First, a description is provided regarding how a seed treatment producer or manufacturer may play a role. Second, the seed applicator's function is described. Finally, a description of the part performed by the seed treatment equipment manufacturer is provided.

Seed Treatment Manufacturer:

The manufacturer of a seed treatment that is conventionally labeled for use and applied at a rate of 3 fl. oz per 100 pounds of seed is re-labeled to include two supplemental pieces of product use instruction and information: 1) a size index ("SI") factor which relates to the conventional rate of application, and 2) a "SIRA" chart which details the size indexed rate adjustment for varied sizes of seeds to be treated. These changes to the label could include these two elements presented in a format similar to that shown in Table 5, below (which is a reproduction of Table 1, discussed above), for a product that has a conventional application rate of 3 fl. oz per 100 pounds of seed, now linked to an SI of 2,800.

TABLE 5

Sample SI and SIRA Chart
SIRA

| Seed Size | | fl. oz per 100 lbs of seed | |
|---|---|---|---|
| Seeds per Pound | 2,100 | 2.2495 | |
| | 2,200 | 2.3566 | |
| | 2,300 | 2.4637 | |
| | 2,400 | 2.5708 | |
| | 2,500 | 2.6780 | |
| | 2,600 | 2.7851 | |
| | 2,700 | 2.8922 | |
| | 2,800 | 3.0000 | SI |
| | 2,900 | 3.1064 | |
| | 3,000 | 3.2136 | |
| | 3,100 | 3.3207 | |
| | 3,200 | 3.4278 | |
| | 3,300 | 3.5349 | |
| | 3,400 | 3.6420 | |
| | 3,500 | 3.7492 | |
| | 3,600 | 3.8563 | |
| | 3,700 | 3.9634 | |
| | 3,800 | 4.0705 | |

Seed Treatment Applicator:

The applicator of the seed treatment product is now presented with new label instructions and may follow such instructions. To implement the new instructions, the applicator determines the seed size of the seed to be treated and then follows conventional calibration and application procedures based on the size indexed rate instructed on the label. For example, if the applicator determines that the seed lot size is 2,100 seeds per pound, then the applicator adjusts the application rate to 2.25 fl. oz/cwt rather than 3.00 fl. oz/cwt as conventionally practiced with the same treatment today. If the applicator's seed lot is sized at 2,800 seeds per pound, then the applicator calibrates and applies the product at 3.00 fl.

oz/cwt. If the applicator's seed lot size is 3,600 seeds per pound, then the application rate is adjusted and calibrated to 3.856 fl. oz/cwt.

Seed Treatment Equipment Manufacturer:

Once the SIRA method of application is introduced to the market, manufacturers of equipment can then focus on the development of equipment features that streamline and simplify the calibration and rate adjustment process.

CLAIMS NOT LIMITED TO DISCLOSED EMBODIMENTS

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

What is claimed is:

1. A seed treatment method comprising:
  (a) obtaining a quantity of seeds from a seed supplier;
  (b) obtaining a seed care product from a seed care product supplier;
  (c) determining a size-adjusted application rate at which to apply said seed care product to said quantity of seeds, wherein said size-adjusted application rate is based on the seed size of said quantity of seeds; and
  (d) applying at least a portion of said seed care product to at least a portion of said quantity of seeds at said size-adjusted application rate to thereby provide treated seeds,
  wherein said determining of step (c) includes acquiring a size index that provides a correlation between seed size and an application rate of said seed care product,
  wherein said acquiring of said size index is carried out by using a Size Index Rate Adjustment ("SIRA") equation provided on or with said seed care product,
  wherein said determining of step (c) includes calculating said size-adjusted application rate by inputting said seed size of said quantity of seeds into said SIRA equation.

2. The method of claim 1, wherein said SIRA equation is provided by said seed care product supplier in conjunction with said seed care product.

3. The method of claim 1, wherein said acquiring of said size index includes reading said SIRA equation.

4. A seed treatment method comprising:
  (a) obtaining a quantity of seeds from a seed supplier;
  (b) obtaining a seed care product from a seed care product supplier;
  (c) determining a size-adjusted application rate at which to apply said seed care product to said quantity of seeds, wherein said size-adjusted application rate is based on the seed size of said quantity of seeds; and
  (d) applying at least a portion of said seed care product to at least a portion of said quantity of seeds at said size-adjusted application rate to thereby provide treated seeds,
  wherein said determining of step (c) includes acquiring a size index that provides a correlation between seed size and an application rate of said seed care product,
  wherein said acquiring of said size index is carried out by inputting said seed size of said quantity of seeds into a Size Index Rate Adjustment ("SIRA") calculator.

5. The method of claim 4, wherein said seed size is determined based on the number of said seeds per a selected unit of weight.

6. The method of claim 4, wherein said seed size is determined by physically measuring the size of at least a portion of said quantity of seeds.

7. The method of claim 4, wherein said determining of step (c) includes acquiring an average seed size of said quantity of seeds.

8. The method of claim 4, wherein said SIRA calculator is provided by said seed care product supplier.

9. The method of claim 4, wherein said seed care product comprises at least one product selected from the group consisting of a fungicide, an insecticide, a nematicide, a rodenticide, an inoculant, a biological pesticide, a cosmetic additive, a flow/plantability additive, a plant growth regulator, a nutritional, a growth enhancer, a dye, a colorant, and combinations thereof.

10. The method of claim 4, wherein said quantity of seeds comprises at least one seed selected from the group consisting of soybeans, corn, sorghum, wheat, barley, oats, rice, cotton, sunflowers, and combinations thereof.

11. The method of claim 4, wherein said SIRA calculator is accessible via the interne.

12. The method of claim 11, wherein said SIRA calculator is an online calculator.

13. The method of claim 4, wherein said size-adjusted application rate calculated by said SIRA calculator is expressed in terms of fluid ounces of seed care product per 100 pounds of seed.

14. The method of claim 4, wherein said SIRA calculator is configured to receive the inputted seed size in terms of number of seeds per given unit of weight, wherein said size-adjusted application rate calculated by said SIRA calculator increases with an increase in said seed size inputted into said SIRA calculator.

15. A method of providing a seed care product, said method comprising:
  (a) obtaining said seed care product;
  (b) determining a plurality of size-adjusted application rates for applying said seed care product to seeds, wherein said size-adjusted application rate is based on the size of said seeds;
  (c) providing said seed care product to an applicator of seed care products; and
  (d) communicating said size-adjusted application rates to said applicator of seed care products,
  wherein said communicating of step (d) comprises supplying a Size Index Rate Adjustment ("SIRA") calculator to said applicator of seed care products,
  wherein said SIRA calculator can be used to calculate said size-adjusted application rate based on a seed size inputted into said SIRA calculator.

16. The method of claim 15, wherein the size of said seeds is based on the number of said seeds per a selected unit of weight.

17. The method of claim 15, wherein the size of said seeds is based on an average of one or more physical dimensions of said seeds.

18. The method of claim 15, wherein said SIRA calculator is accessible to said applicator via the internet.

19. The method of claim 18, wherein said SIRA calculator is an online calculator.

20. The method of claim 15, wherein steps (c) and (d) are carried out by the same party.

21. The method of claim 15, wherein said size-adjusted application rate calculated by said SIRA calculator is expressed in terms of fluid ounces of seed care product per 100 pounds of seed.

22. The method of claim 15, wherein said SIRA calculator is configured to receive the inputted seed size in terms of number of seeds per given unit of weight, wherein said size-adjusted application rate calculated by said SIRA calculator increases with an increase in said seed size inputted into said SIRA calculator.

23. A method of providing a seed care product, said method comprising:
(a) obtaining said seed care product;
(b) determining a plurality of size-adjusted application rates for applying said seed care product to seeds, wherein said size-adjusted application rate is based on the size of said seeds;
(c) providing said seed care product to an applicator of seed care products; and
(d) communicating said size-adjusted application rates to said applicator of seed care products,
wherein said communicating of step (d) comprises supplying a Size Index Rate Adjustment ("SIRA") equation to said applicator of seed care products,
wherein said SIRA equation can be used to calculate said size-adjusted application rate based on a seed size inputted into said SIRA equation.

24. The method of claim 23, wherein said SIRA equation is printed on a label provided with said seed care product.

25. The method of claim 15, wherein said obtaining of step (a) comprises manufacturing said seed care product.

26. The method of claim 15, wherein said seed care product comprises a fungicide, an insecticide, a nematicide, a rodenticide, an inoculant, a biological pesticide, a cosmetic additive, a flow/plantability additive, a plant growth regulator, a nutritional, a growth enhancer, a dye, and/or a colorant.

27. The method of claim 15, wherein said applicator of said seed care products is a seed distributor, a seed retailer, or a farm operation.

28. The method of claim 23, wherein step (c) and (d) are carried out by the same party.

29. A seed treatment method comprising:
(a) obtaining a quantity of seeds from a seed supplier;
(b) obtaining a seed care product from a seed care product supplier;
(c) determining a size-adjusted application rate at which to apply said seed care product to said quantity of seeds, wherein said size-adjusted application rate is based on the seed size of said quantity of seeds; and
(d) applying at least a portion of said seed care product to at least a portion of said quantity of seeds at said size-adjusted application rate to thereby provide treated seeds,
wherein said seed size is based either on the number of said seeds per a selected unit of weight or by physical measurement of the size of at least a portion of said quantity of seeds,
wherein said determining of step (c) includes a using a Size Index Rate Adjustment ("SIRA") calculator provided by said seed care product supplier to calculate said size-adjusted application rate based at least in part on a seed size inputted into said SIRA calculator.

30. The method of claim 29, wherein said determining of step (c) includes acquiring an average seed size of said quantity of seeds.

31. The method of claim 29, wherein said seed care product comprises at least one product selected from the group consisting of a fungicide, an insecticide, a nematicide, a rodenticide, a plant growth regulator, a nutritional, a growth enhancer, a dye, and a colorant, and combinations thereof, wherein said quantity of seeds comprises at least one seed selected from the group consisting of soybeans, corn, sorghum, wheat, barley, oats, rice, cotton, sunflowers, and combinations thereof.

32. The method of claim 29, wherein said SIRA calculator is accessible via the internet.

33. The method of claim 32, wherein said SIRA calculator is an online calculator.

34. The method of claim 29, wherein said size-adjusted application rate calculated by said SIRA calculator is expressed in terms of fluid ounces of seed care product per 100 pounds of seed.

35. The method of claim 29, wherein said SIRA calculator is configured to receive the inputted seed size in terms of number of seeds per given unit of weight, wherein said size-adjusted application rate calculated by said SIRA calculator increases with an increase in said seed size inputted into said SIRA calculator.

* * * * *